(12) United States Patent
Zoromski et al.

(10) Patent No.: US 7,465,777 B2
(45) Date of Patent: Dec. 16, 2008

(54) HYBRID POLYMER MATERIALS FROM REACTIVE EXTRUSION FOR MEDICAL DEVICES

(75) Inventors: Michele L. Zoromski, Minneapolis, MN (US); Liliana L. Atanasoska, Edina, MN (US); Robert W. Warner, Woodbury, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 449 days.

(21) Appl. No.: 11/366,230

(22) Filed: Mar. 2, 2006

(65) Prior Publication Data

US 2007/0208155 A1 Sep. 6, 2007

(51) Int. Cl.
*C08G 77/442* (2006.01)
*C08G 77/02* (2006.01)

(52) U.S. Cl. .................. 528/27; 525/100; 525/104; 525/106; 525/285; 528/39

(58) Field of Classification Search .................. None
See application file for complete search history.

(56) References Cited

U.S. PATENT DOCUMENTS

| | | | |
|---|---|---|---|
| 5,252,654 A | 10/1993 | David et al. | |
| 5,264,260 A | 11/1993 | Saab | |
| 5,270,086 A | 12/1993 | Hamlin | |
| 5,290,306 A | 3/1994 | Trotta et al. | |
| 5,304,340 A | 4/1994 | Downey | |
| 5,306,246 A | 4/1994 | Sahatjian et al. | |
| 5,328,468 A | 7/1994 | Kaneko et al. | |
| 5,330,428 A | 7/1994 | Wang et al. | |
| 5,554,120 A | 9/1996 | Chen et al. | |
| 5,556,383 A | 9/1996 | Wang et al. | |
| 5,587,125 A | 12/1996 | Roychowdhury | |
| 5,647,848 A | 7/1997 | Jorgensen | |
| 5,849,215 A | 12/1998 | Gin et al. | |
| 5,948,946 A | 9/1999 | Harmer et al. | |
| 6,024,722 A | 2/2000 | Rau et al. | |
| 6,160,190 A | 12/2000 | Harmer et al. | |
| 6,242,063 B1 | 6/2001 | Ferrera et al. | |
| 6,284,333 B1 | 9/2001 | Wang et al. | |
| 6,328,925 B1 | 12/2001 | Wang et al. | |
| 6,730,377 B2 | 5/2004 | Wang | |
| 6,737,145 B1 | 5/2004 | Watanabe et al. | |
| 6,765,059 B2 | 7/2004 | Corley | |
| 6,825,260 B2 | 11/2004 | Sievers et al. | |
| 6,905,743 B1 | 6/2005 | Chen et al. | |
| 2003/0236513 A1 | 12/2003 | Schwartz et al. | |
| 2003/0236514 A1 | 12/2003 | Schwartz | |
| 2005/0064223 A1 | 3/2005 | Bavaro et al. | |
| 2005/0215728 A1* | 9/2005 | Cao et al. .................. 525/342 |

FOREIGN PATENT DOCUMENTS

| | | |
|---|---|---|
| WO | WO 01/017575 A1 | 3/2001 |
| WO | WO 02/100559 A1 | 12/2002 |
| WO | WO 2005/019315 A1 | 3/2005 |

OTHER PUBLICATIONS

International Search Report (6 pgs.).
Bhattacharyya, "Reactively compatibilised polyamide6/ethylene-co-vinyl acetate blends: mechanical properties and morphology," 2005, Polymer 46, pp. 1661-1674.
Arostegui, "Critical inter-particle distance dependence and super-toughness in poly(butylene terephthalate)/grafted poly(ethylene-octene) copolymer blends by means of polyarylate addition," 2003, Polymer 44, pp. 5227-5237.
Tomova, "Phase behavior in ternary polyamide 6/polyamide 66/elastomer blends," 2000, Polymer 41, pp. 7773-7783.
Wu, "Polyethylene-octene elastomer/silica hybrids prepared by a sol-gel process using tetraethoxysiliane," 2003, Designed Monomers and Polymers, vol. 6, No. 4, pp. 369-381.
Wu, "Modification of Polyethylene-Octene Elastomer by Silica Through a Sol-Gel Process," 2003, Journal of Applied Polymer Science, vol. 88, pp. 966-972.
Wu, "In situ Polymerization of Silicic Acid in Polyethylene-Octene Elastomer: Properties and Characterization of the Hybrid Nanocomposites," 2003, Journal of Polymer Science: Part B: Polymer Physics, vol. 41, pp. 351-359.
G'Sell, "Polypropylene/polyamide 6/polyethylene-octene elastomer blends. Part 2: volume dilation during plastic deformation under uniaxial tension," 2004, Polymer 45, pp. 5785-5792.
Krump, "Preparation of a maleated Fischer-Tropsch paraffin wax and FTIR analysis of grafted maleic anhydride," 2005, Polymer Testing 24, pp. 129-135.

* cited by examiner

*Primary Examiner*—Marc S Zimmer
(74) *Attorney, Agent, or Firm*—Brooks, Cameron & Huebsch, PLLC

(57) ABSTRACT

The present disclosure relates to hybrid polymers, methods of making such hybrid polymers, and medical devices that include the hybrid polymers. Such hybrid polymers are suitable for forming biomaterials in a predetermined shape for use in medical devices and medical device components. The hybrid polymers of the present disclosure are formed through a reactive extrusion process prior to being formed into the predetermined shape of the medical device or medical device component.

24 Claims, No Drawings

HYBRID POLYMER MATERIALS FROM REACTIVE EXTRUSION FOR MEDICAL DEVICES

BACKGROUND OF THE DISCLOSURE

The combination of polymers and ceramics in hybrid materials is an active area of materials research. These composite materials join the benefits of polymers, such as flexibility, toughness, and ease of processing, with those of ceramics, such as hardness, durability, and thermal stability. By modifying the selection and ratios of the polymers and ceramics, hybrid materials having a wide variety of structural and chemical characteristics can be formed. This can be of significant utility in the medical device arena.

Nanotechnology is an emerging field that uses the principles of science and engineering to fabricate materials or structures of dimensions in the nanometer scale. Some nanostructures currently under investigation include quantum dots and wires, nanoscale self-assemblies and thin films, nanocrystals, nanotubes, nanowires, nanorods, nanofoams, nanospheres and nanofibers. The nanoscale materials can display unusual and unique property profiles as compared to macromaterials. Physical, chemical and biological properties such as unique shape, orientation, surface chemistry, topology and reactivity exhibited by these materials originate from their small dimensions. These material properties can translate into unusual electrical, optical, magnetic, mechanical, thermal and biological properties for these materials.

Currently medical device catheters, and other types of medical devices where a smaller size is preferred, have a need to further reduce size and mass. This reduction in size and mass may allow for enhanced product performance leading to minimized patient trauma and recovery time. Attempts have been made to incorporate ceramic nanostructures into polymer matrices for the purpose of improving both the durability and surface characteristics (e.g., abrasion resistance) of the hybrid polymer. However, traditional nanostructures have been difficult to effectively incorporate into the polymer matrix. A suitable solution to this problem is desired.

DETAILED DESCRIPTION OF DISCLOSURE

The present disclosure provides hybrid polymers, methods of making such hybrid polymers, and medical devices that include the hybrid polymers. Such hybrid polymers are suitable for forming biomaterials in a predetermined shape for use in medical devices and medical device components. The hybrid polymers of the present disclosure are formed through a reactive extrusion process prior to being formed into the predetermined shape of the medical device or medical device component.

The present disclosure provides, among other things, methods for making the hybrid polymer through a reactive extrusion process during a melt extrusion. The hybrid polymer produced by this method includes sol-gel preparations dispersed through and covalently attached to a polymer during the reactive extrusion process in such a way that prevents separation of the sol-gel preparations from the polymer. The resulting hybrid polymer of the present disclosure should have increased impact strength, and tensile strength, while minimizing the impact on modulus and crystallinity of the polymer.

The present invention provides for a reactive extrusion process of an organic polymer (e.g., polyolefins) and a sol-gel preparation(s). As used herein, a "reactive extrusion process" is the use of chemical reactions during a polymer extrusion process to form desired products. Specifically, the present disclosure provides for, in one embodiment, grafting of a cyclic anhydride onto the organic polymer followed by covalently coupling the inorganic sol-gel structures to the organic polymer during a single pass of the reactive extrusion process. In an additional embodiment, it is also possible to covalently couple the inorganic sol-gel structures to a polymer already having a grafted cyclic anhydride during a single pass of the reactive extrusion process.

Free radical initiators, crosslinking agents, and other reactive additives can be injected into the reactive extrusion process to cause and/or promote the grafting reactions discussed herein. In addition, while the reactive extrusion process may result in production of a homogeneous product, a somewhat heterogeneous product is within the scope of this disclosure. Examples of such processes and/or techniques include, but are not limited to, mixing process that include screw extrusion (single or twin barrel), among others.

In addition, the medical devices and/or medical device components in the predetermined shape formed from the hybrid polymer of the present disclosure are further characterized in that they can be substantially insoluble in body fluids and tissues and is designed and constructed to be placed in or onto the body or to contact fluid or tissue of the body. Ideally, the hybrid polymer will be biostable, biocompatible, and will not induce reactions in the body such as blood clotting, tissue death, tumor formation, allergic reaction, foreign body reaction (rejection) or inflammatory reaction; will have the physical properties such as strength, elasticity, permeability and flexibility required to function for the intended purpose; can be purified, fabricated and sterilized; and will substantially maintain its physical properties and function during the time that it remains implanted in or in contact with the body. For the purpose of this disclosure, a "biostable" material is one that is not broken down by the body, whereas a "biocompatible" material is one that is not rejected by the body.

As used herein, a "medical device" and/or "medical device component" may be defined as a device or device component, respectively, having a predetermined shape with surfaces that contact blood or other body fluids and/or tissues in the course of their operation. This can include, for example, extracorporeal devices for use in surgery such as blood oxygenators, blood pumps, blood sensors, tubing used to carry blood and the like which contact blood which is then returned to the patient. This can also include implantable devices such as vascular grafts, stents, electrical stimulation leads, valves for use in the cardiac system (e.g., heart valves), orthopedic devices, elongate catheters (e.g., guide catheters, balloon catheters, stent delivery catheters), catheter shaft components, filters, guide wires, shunts, sensors, membranes, dilatation balloons, replacement devices for nucleus pulposus, cochlear or middle ear implants, intraocular lenses, coatings for such devices, and the like.

The hybrid polymer of the present disclosure can be used in medical devices as well as nonmedical devices. As discussed, they can be used in medical devices and medical device components, and are suitable as biomaterials. Examples of medical devices are listed herein. Examples of nonmedical devices include foams, insulation, clothing, footwear, paints, coatings, adhesives, and building construction materials, besides others.

As used herein, the terms "a," "an," "the," "one or more," and "at least one" are used interchangeably and include plural referents unless the context clearly dictates otherwise. Unless defined otherwise, all scientific and technical terms are understood to have the same meaning as commonly used in the art to which they pertain. For the purpose of the present invention, additional specific terms are defined throughout.

The melt extruder used in the reactive extrusion process of the present disclosure is designed to conduct several operations during the preparation of the melt reactive extrusion. The hybrid polymers of the present disclosure are produced in the reactive extrusion process. It is desired according to the present disclosure to blend or mix the organic polymer, the cyclic anhydride, a free radical source, and the sol-gel preparations in an extruder, such as a single-screw or twin-screw extruder under appropriate temperature and shear/pressure conditions to ensure mixing.

A particularly desirable reaction device is an extruder having one or more ports. For example, the reaction device is a co-rotating, twin-screw extruder, that allows multiple feeding and venting ports and provides high intensity distributive and dispersive mixing that is essential to produce grafted polymers of uniform composition and homogeneous distribution of the sol-gel preparations in the organic polymer. The reactions are desirably conducted in the polymer melt phase; i.e., in the absence of bulk solvent. This is a highly effective process since the solvent removal step is not needed in the process.

In one embodiment, the organic polymer is fed into and melted in the melt extruder. After melting the organic polymer, the cyclic anhydride is fed into and melt blended in the melt extruder and, further down the extruder barrel, the free radical source, such as a peroxide, is fed to the extruder to yield improved grafting efficiency of the cyclic anhydride to the organic polymer. As discussed herein, it is also possible to begin the process with a polymer that has already has a grafted cyclic anhydride. Examples of such polymers include, but are not limited to, poly(ethylene oxide)-grafted-polyelectrolyte poly(sodium acrylate) (PEO-g-PAA), and those sold under the trade designator "Fusabond," such as Fusabond N 493D (DuPont, Wilmington Del.). The use of other polymers having grafted cyclic anhydride groups is also possible.

After a length of extrusion sufficient to accomplish organic polymer grafting of the cyclic anhydride, i.e., sufficient time, the sol-gel preparations are fed to the molten, grafted organic polymer stream either as pellets or powder through an open throat to the extruder or as a molten stream fed through a side stream extruder. After melt consolidation of the grafted polymer and the sol-gel preparations, a vacuum port can optionally be used to remove ungrafted or unreacted cyclic anhydride. The resulting hybrid polymer can then be processed in a number of ways, including being extruded through die(s), injection molded or blow molded into the predetermined shape. In addition, the resulting hybrid polymer can also be coated onto or coextruded with a substrate in forming the medical device component.

By grafting the cyclic anhydrides onto the organic polymer, the resulting grafted organic polymer is more compatible with and reactive to the sol-gel preparations. The compatibility of the grafted organic polymer of the present invention with the sol-gel preparations can be controlled by the selection of the cyclic anhydride, the level of grafting and the blending process conditions. Tailoring the compatibility of the modified organic polymer with the sol-gel preparations leads to better processability and improved physical properties of the resulting hybrid polymer.

The organic polymers suitable for use in forming the cyclic anhydride grafted polymer of the present invention include a polymer such as, but not limited to, polyolefins, polystyrene, polybutylteraphalate (PBT), fluoropolymers, polyamides, co-block polymers such as PEBAX®, ethylene vinyl acetate (EVA), and mixtures thereof. The term "polyolefin" refers to a polymer which may be also described as "a saturated hydrocarbon;" its backbone and side-chains are composed solely of units of saturated carbon atoms having only hydrogen (or deuterium) attached. A "polyolefin" includes those saturated hydrocarbon polymers produced by free radical, organometallic, or other known methods of polymerization of olefins, and includes, for example, polyethylene, polypropylene, poly-1-butene, and poly-4-methyl-1-pentene.

It also includes random copolymers of these with other olefin monomers such as isobutylene, 1-pentene, 1-hexene, 1-octene, 1-dodecene, 4-vinyl cyclohexane, 4-vinyl cyclohexene, cycloalkenes such as cyclohexene, norbornylene, and the like, and also includes, for example, diene monomers such as butadiene, isoprene, cyclodienes such as cyclopentadiene, dicyclopentadiene, norbornyldiene, and the like, which, following polymerization and hydrogenation, yield "olefin polymers" often described in the art as "polyolefins." Included are the ethylene/alpha-olefin, such as ethylene-propylene, copolymers, and the ethylene copolymers with 1-butene, 1-hexene, 1-pentene, 1-octene (e.g., polyethylene-octene elastomer (POE)), and 4-methyl-1-pentene, including those high ethylene content copolymers commonly referred to as linear, low-density polyethylenes as well as those containing lesser amounts of ethylene. Polyolefins include polypropylene, propylene copolymers, or an ethylene/alpha-olefin random copolymer, for example an ethylene/propylene copolymer. Polypropylene polymers and its copolymers may be isotacetic, syndiotacetic, or atacetic.

The molecular weights of the organic polymer used for the hybrid polymer may vary depending on the desired properties and use. In addition, the weight percent of organic polymer content of the hybrid polymer according to the present disclosure may also vary depending on the desired properties and use. For example, the cyclic anhydrides content of the hybrid polymer according to the present disclosure can be from about 0.1 to about 20.0 weight percent, preferably from about 0.1 to about 5.0 weight percent. The molecular weights of the cyclic anhydrides useful for making the hybrid polymer may also vary depending on the desired properties and use. In addition, the organic polymer content of the hybrid polymer according to the present disclosure is about 60 to 100 weight percent, preferably 80 to 95 weight percent.

Examples of cyclic anhydrides useful for making the cyclic anhydride grafted polymer for the hybrid polymer according to the present disclosure include maleic anhydride, succinic anhydride, hexahydrophthalic anhydride, tetrahydrophthalic anhydride, dodecylsuccinic anhydride, phthalic anhydride, nadic anhydride, pyromellitic anhydride, and mixtures thereof. A cyclic anhydride, which is particularly useful in certain embodiments of the disclosure, is maleic anhydride (Aldrich Chemical Company, CAS#108-31-6).

It is also possible to use other compounds in addition to the ones provided herein, either alone or in combination, for covalently coupling the inorganic sol-gel structures to the organic polymer. Examples of such compounds include, but are not limited to, fumaric acid, silicic acid, acrylic acid, epoxy grafted polymers, and polyanhydrides.

The free radical source suitable for use in the process of the present disclosure are those materials typically used for the organic polymers provided herein that exhibit free radical generation in the melt processing range typically used for organic polymers. Specific examples include acyl peroxides, such as benzoyl peroxide; dibenzoyl peroxide, dialkyl, diaryl, or aralkyl peroxide, such as di-t-butyl peroxide; dicumyl peroxide; cumyl butyl peroxide; 1,1-di-t-butyl peroxy-3,5,5-trimethylcyclohexane; 2,5-dimethyl-2,5-di(t-butylperoxy)hexane; 2,5-dimethyl-2,5-bis-(t-butylperoxy)hexyne-3 and bis (a-t-butyl peroxyisopropylbenzene); peroxyesters such as t-butyl peroxypivalate; t-butyl peroctoate; t-butyl perbenzoate; 2,5-dimethylhexyl-2,5-di(perbenzoate) t-butyl di(perphthalate); dialkyl peroxymonocarbonates and peroxydicarbonates; hydroperoxides, such as t-butyl hydroperoxide, p-methane hydroperoxide, pinane hydroperoxide and cumene hydroperoxide and ketone peroxides, such as cyclohexanone peroxide, methyl ethyl ketone peroxide, and the like.

The free radical source is generally used in the process according to the present disclosure in a sufficient quantity to make it possible to effect the grafting. Furthermore, it is desirable that the quantity should not exceed the minimum quantity needed because any excess of radical-generator may results in a degradation of the organic polymer and/or may create undesirable cross-linking of the organic polymer.

The sol-gel preparations of the present disclosure can be formed from at least one silicon alkoxide, where the resulting sol-gel preparations can be bonded to the grafted organic polymer. In one embodiment, the sol-gel preparations are formed from at least one silicon alkoxide of the formula (Formula I):

$$Si(OR)_4$$

where R is an organic group. Examples of such organic groups include a straight chain or branched alkyl group, a straight chain or branched alkylene group, where R optionally includes heteroatoms that may be in the chain of the organic group or pendant therefrom as in a functional group.

In an alternative embodiment, the sol-gel preparations can be selected from the group consisting of metal alkoxides, metal acetates, metal salts of short and long chain fatty acids (e.g., $M(OOCR)x$, where R is an organic group, as discussed herein, and x is dependent on the oxidation state of the metal, M), and metal salt of acetyl acetonate.

As used herein, the term "organic group" is used for the purpose of this disclosure to mean a hydrocarbon group that is classified as an aliphatic group. In the context of the present disclosure, suitable organic groups for the silicon alkoxide of this disclosure are those that do not interfere with the formation of sol-gel preparations. In the context of the present disclosure, the term "aliphatic group" means a saturated or unsaturated linear or branched hydrocarbon group. This term is used to encompass alkyl (e.g., —$CH_3$, which is considered a "monovalent" group) (or alkylene if within a chain such as —$CH_2$—, which is considered a "divalent" group), alkenyl (or alkenylene if within a chain), and alkynyl (or alkynylene if within a chain) groups, for example. The term "alkyl group" means a saturated linear (i.e., straight chain), or branched monovalent hydrocarbon group including, for example, methyl, ethyl, n-propyl, isopropyl, t-butyl, amyl, heptyl, dodecyl, octadecyl, 2-ethylhexyl, and the like. The term "alkenyl group" means an unsaturated, linear or branched monovalent hydrocarbon group with one or more olefinically unsaturated groups (i.e., carbon-carbon double bonds), such as a vinyl group. The term "alkynyl group" means an unsaturated, linear or branched monovalent hydrocarbon group with one or more carbon-carbon triple bonds. The term "heteroatom" means an element other than carbon (e.g., fluorine, nitrogen, oxygen, sulfur, chlorine, etc.).

In one embodiment, each R is independently a straight chain or branched alkyl group optionally including heteroatoms, such as nitrogen, oxygen, phosphorus, sulfur, and halogen. The heteroatoms can be in the backbone of R or pendant therefrom, and they can form functional groups such as heteroatom-containing groups (e.g., functional groups) include, for example, an alcohol, carbonyl, ether, acetoxy, ester, aldehyde, acrylate, amine, amide, imine, imide, and nitrile, whether they be protected or unprotected. In one embodiment, R does not include heteroatoms. In an additional embodiment, each R is independently a straight chain or branched alkyl group includes 18 carbon atoms or less. In a further embodiment, each R is independently a straight chain or branched (C2-C8) alkyl group. In other embodiments, each R is independently a straight chain or branched (C2-C4) alkyl group (e.g., ethyl, n-propyl, isopropyl, or butyl). In one example, R is a C2 alkyl group.

As will be appreciated, for Formula I, R can vary within any one of the sol-gel preparations. For example, in addition to each R being the same or different within each $Si(OR)_4$, the OR groups can be the same or different in any one sol-gel preparation.

Although certain sol-gel preparations are described herein, the sol-gel preparations used in the present disclosure can be formed in a cross-linking process from a wide variety of silicon alkoxides of Formula I. For example, a method of preparing the sol-gel preparations involves the combining of at least one silicon alkoxide of the Formula I under sol-gel reaction conditions to form a reaction mixture allowing the sol-gel preparations to form in the reaction mixture.

The Sol-gel processes is generally described, for example, in "Sol-Gel Science: The Physics and Chemistry of Sol-Gel Processing" (Brinker et al., Academic Press, 1990). As used herein, "sol-gel" refers to any method of synthesizing the sol-gel preparations that comprises a step wherein at least one of the precursors is an aqueous or organic dispersion, sol, or solution.

Three reactions are generally used to describe the sol-gel process: hydrolysis, alcohol condensation, and water condensation. The characteristics and properties of the sol-gel preparations formed through the sol-gel process with compounds of Formula I can be related to a number of factors that affect the rate of hydrolysis and condensation reactions, such as, pH, temperature and time of reaction, reagent concentrations, catalyst nature and concentration, aging temperature and time, and drying. Controlling these factors allow for the structure and properties of the sol-gel preparations to be varied as desired.

A method for preparing the sol-gel preparations for the present disclosure through a sol-gel process involves the combining of (1) the mixture of the compound(s) of Formula I and (2) an aqueous or organic dispersion or sol of reagents that include at least one alcohol and a catalyst provided under conditions for the sol-gel reaction to take place. Examples of silicon alkoxides of Formula I include normal and branched butoxides, propoxides, ethoxides, and methoxides. Specific examples of suitable silicon alkoxide of Formula I include tetraethoxysilane (TEOS). Specific examples of suitable metal alkoxides include titanium isopropoxide (TMOS), titanium (IV) n-butoxide, titanium (IV) t-butoxide, titanium (IV) ethoxide, tantalum (V) ethoxide, tantalum (V) methoxide, and tantalum (V) trifluoroethoxide. The use of other metal alkoxides is also possible.

In an additional embodiment, the sol-gel preparations for the present disclosure can further include non-metallic carbon alkoxide and silsesquioxane (POSS) carbon nanotubes that have been covalently attached to alkoxy silane. For example, the carbon nanotubes can include alcohol (—OH) and/or isocyanate (—N=C=O) functional groups that can react with functionalized alkoxy silanes such as $(RO)_3Si$—R—N=C=O (functionalized with an isocyanate) and/or $(RO)_3Si$—R—$NH_2$ (functionalized with a primary or secondary amine) and/or with the alkoxy silanes having additional functional groups in a sol-gel reaction.

Examples of suitable catalysts include mineral acids such as hydrochloric acid (HCl), ammonia, acetic acid, potassium hydroxide (KOH), titanium alkoxides, vandium alkoxides, amines, KF, and HF. Additionally, it has been observed that the rate and extent of the hydrolysis reaction is most influenced by the strength and concentration of the acid- or base catalyst. In one embodiment, the concentration of the acid- or base-catalyst can be from 0.01 M to 7M. In addition, the nature of the sol-gel reaction can be influenced by the selection of an acid or base catalyst, where under acid-catalyzed conditions the sol-gel reaction yields primarily linear or randomly branched polymers which entangle and form additional branches resulting in gelation. On the other hand, the sol-gel reaction yields derived under base-catalyzed conditions can yield more highly branched clusters which behave more like discrete clusters.

Examples of suitable alcohols include anhydrous alcohol such as methanol, ethanol, propanol, butanol, pentanol, and mixtures thereof. Suitable alcohols have a water content of less than about 1% by weight, especially less than about 0.5% by weight or less than about 0.1% by weight. Other organic solvent (or mixtures of solvents) may also be used that are miscible with the other components.

According to the present disclosure, the sol-gel reaction can take place with the reagents in either a liquid phase, a semi-liquid phase, and/or a gas phase. In one embodiment, in the liquid phase a suitable solvent would include tetrahydrofuran (THF, Aldrich Chemical Company, CAS# 109-99-9). Typical reaction conditions for the sol-gel reaction can occur in a temperature range of 20° C. to 100° C. Other temperature ranges are also possible.

Such methods are exemplary only. The present disclosure is not limited by the methods described herein for making the sol-gel preparations derived from the compounds of Formula I.

The method of forming the medical device and/or medical device component can then include (1) preparing the hybrid polymer in the reactive extrusion process with the cyclic anhydride grafted polymer and the sol-gel preparation, and (2) forming the hybrid polymer prepared from the extrusion into the predetermined shape of the medical device component. As discussed herein, preparing the hybrid polymer in the reactive extrusion process includes combining the sol-gel preparations with the grafted polymer during the melt process to form the hybrid polymer.

The hybrid polymer may contain a sufficient amount by weight percent of the sol-gel preparations that do not interfere with either the sol-gel preparations and/or the processing of the hybrid polymer.

The hybrid polymer of the present disclosure can be utilized in several different ways: 1) on its own, (2) combined with one or more additional thermoplastics (co-block polymers—PEBAX®, polyamides), PET, PBT, etc. to alter the final properties of the hybrid polymer. Furthermore, other components known in the art may be added to the graft polymers of this invention to further enhance the properties of the final material. All of these additives are generally used in relatively small amounts as compared to the weight percent of the final composition. Applications for the reactive extruded hybrid polymer produced according to the present disclosure include films, injection molded articles, extruded profiles, fiber additives, and barrier containers.

Suitable polymers can have a viscosity and molecular weights suitable for blending and/or melt processing, as discussed herein. In addition to the polymers described herein, the hybrid polymers of the disclosure can also include a variety of additives. These can include antioxidants, colorants, processing lubricants, stabilizers, imaging enhancers, fillers, and the like. The present disclosure also provides polymers and compounds used to form such polymers, and biomaterials formed from such polymers that can be used in medical devices.

Additional additives can also include, but are not limited to, metal alkoxides $M(OR_2)_n$, where the value for n is dependent on the oxidation state of the metal M, and $R_2$ is an organic group as discussed herein. In one embodiment, the metal alkoxides can be incorporated into mixture of Formula I the prior to the sol-gel process. M can be selected from the group of metals consisting of Groups 2, 4, 5, 8, 9, 13, 14 and 15. For example, M can be selected from the group of metals consisting of Si, Fe, Ti, Zr, Ir, Ru, Bi, Ba, Al, Ta, and Sr. In an alternative embodiment, the examples of M elements can include non-metal element C and a polyhedral oligomeric silsesquioxane (POSS). Addition of the additives such as the metal alkoxide can then be used in the sol-gel process to modify the nature of the resulting hybrid polymer.

A ThermoHaake PolyLab Mixer rheometer system equipped with a Rheocord base unit and a RheoMix measuring mixer was set-up to process the samples provided in Table 1. The RheoMix mixer was operated at a temperature of 160° C. and a mixing speed of 50 rpm. Fusabond N-493D, in amounts provided in Table 1 below, was prepared as a melt in the RheoMix measuring mixer. A sol-gel solution of premixed TEOS, THF and HCl, in the amounts provided in Table 1, was then fed into the melt of the Fusabond N-493D according to Table 1. The Fusabond N-493D of each sample was then mixed with the sol-gel solution for 12.5 minutes. The samples were removed from the RheoMix measuring mixer and allowed to dry.

TABLE 1

Reactants and Percentages by Weight of $SiO_2$ in four (4) samples.

| | $SiO_2$ Content (% by weight) | | | |
|---|---|---|---|---|
| Reactants | 0% by weight | 3% by weight | 6% by weight | 9% by weight |
| POE-g-MAH(g) (Fusabond N-493D) | 31.69 g | 38.55 g | 35.15 g | 31.72 g |
| TEOS (ml) | 0 | 4.42 ml | 8.33 ml | 11.67 ml |
| THF (ml) | 0 | 4.64 ml | 8.74 ml | 12.24 ml |
| 0.25M HCl (ml) | 2.1 ml | 0.78 ml | 1.5 ml | 2.1 ml |

The invention has been described with reference to various specific and preferred embodiments. It is understood, however, that there are many extensions, variations, and modification on the basic theme of the present invention beyond that shown in the detailed description, which are within the spirit and scope of the present invention.

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments set forth herein and that such embodiments are presented by way of example only with the scope of the disclosure intended to be limited only by the claims set forth herein as follows.

What is claimed is:

1. A medical device component comprising a hybrid polymer in a predetermined shape, the hybrid polymer formed during a reactive extrusion of a cyclic anhydride grafted polymer and a sol-gel preparation.

2. The medical device component of claim 1, where the cyclic anhydride grafted polymer is selected from the group consisting of a cyclic anhydride grafted polyether amide, a cyclic anhydride grafted polyethylene, a cyclic anhydride grafted polyethylene-octene elastomer, a cyclic anhydride grafted polypropylene, a cyclic anhydride grafted polystyrene, a cyclic anhydride grafted polybutylteraphalate, a cyclic anhydride grafted fluoropolymer, a cyclic anhydride grafted polyamides, a cyclic anhydride grafted ethylene vinyl acetate, and mixtures thereof.

3. The medical device component of claim 1, where the cyclic anhydride grafted polymer is selected from the group consisting of a maleic anhydride grafted polymer, a succinic anhydride grafted polymer, a hexahydrophthalic anhydride grafted polymer, a tetrahydrophthalic anhydride grafted polymer, a dodecylsuccinic anhydride grafted polymer, a phthalic anhydride grafted polymer, a nadic anhydride grafted polymer, a pyromellitic anhydride grafted polymer, and mixtures thereof.

4. The medical device component of claim 1, where the cyclic anhydride grafted polymer is a maleic anhydride-grafted polyethylene-octene elastomer.

5. The medical device component of claim 1, where the sol-gel preparation is prepared through a sol-gel reaction from compounds selected from the group consisting of tetraethyoxysilane, titanium isopropoxide, titanium (IV) n-butoxide, titanium (IV) t-butoxide, titanium (IV) ethoxide, tantalum (V) ethoxide, tantalum (V) methoxide, and tantalum (V) trifluoroethoxide, and mixtures thereof.

6. The medical device component of claim 1, where the extrusion is screw extrusion.

7. The medical device component of claim 1, where the predetermined shape is formed through injection molding.

8. The medical device component of claim 1, where the predetermined shape is formed through blow molding.

9. The medical device component of claim 1, where the predetermined shape is a coating on a substrate.

10. The medical device component of claim 9, where the coating is coextruded with the substrate.

11. The medical device component of claim 1, where the predetermined shape is a dilatation balloon.

12. The medical device component of claim 1, where the predetermined shape is an elongate catheter.

13. A method of forming a medical device component, the method comprising:

preparing a hybrid polymer in a reactive extrusion of a cyclic anhydride grafted polymer and a sol-gel preparation; and forming the hybrid polymer prepared from the extrusion into a predetermined shape of the medical device component.

14. The method of claim 13, where preparing the hybrid polymer in the reactive extrusion includes combining the sol-gel preparation and the cyclic anhydride grafted polymer in a melting process.

15. The method of claim 14, where combining the sol-gel preparation and the cyclic anhydride grafted polymer includes preparing the hybrid polymer in a screw extruder.

16. The method of claim 13, where forming the hybrid polymer into the predetermined shape includes injection molding the hybrid polymer into the predetermined shape.

17. The method of claim 13, where forming the hybrid polymer into the predetermined shape includes blow molding the hybrid polymer into the predetermined shape.

18. The method of claim 13, where forming the hybrid polymer into the predetermined shape includes forming the hybrid polymer into a dilatation balloon.

19. The method of claim 13, where forming the hybrid polymer into the predetermined shape includes forming the hybrid polymer into an elongate catheter.

20. The method of claim 13, where forming the hybrid polymer into the predetermined shape includes forming the hybrid polymer into a coating on a substrate.

21. The method of claim 13, where the cyclic anhydride grafted polymer is selected from the group consisting of a cyclic anhydride grafted polyether amide, a cyclic anhydride grafted polyethylene, a cyclic anhydride grafted polyethylene-octene elastomer, a cyclic anhydride grafted polypropylene, a cyclic anhydride grafted polystyrene, a cyclic anhydride grafted polybutylteraphalate, a cyclic anhydride grafted fluoropolymer, a cyclic anhydride grafted polyamides, a cyclic anhydride grafted ethylene vinyl acetate, and mixtures thereof.

22. The method of claim 13, where the cyclic anhydride grafted polymer is selected from the group consisting of a maleic anhydride grafted polymer, a succinic anhydride grafted polymer, a hexahydrophthalic anhydride grafted polymer, a tetrahydrophthalic anhydride grafted polymer, a dodecylsuccinic anhydride grafted polymer, a phthalic anhydride grafted polymer, a nadic anhydride grafted polymer, a pyromellitic anhydride grafted polymer, and mixtures thereof.

23. The method of claim 13, where the cyclic anhydride grafted polymer is a maleic anhydride-grafted polyethylene-octene elastomer.

24. The method of claim 13, where the sol-gel preparation is prepared through a sol-gel reaction from compounds selected from the group consisting of tetraethyoxysilane, titanium isopropoxide, titanium (IV) n-butoxide, titanium (IV) t-butoxide, titanium (IV) ethoxide, tantalum (V) ethoxide, tantalum (V) methoxide, and tantalum (V) trifluoroethoxide, and mixtures thereof.

* * * * *